US008795247B2

(12) United States Patent
Bennett et al.

(10) Patent No.: US 8,795,247 B2
(45) Date of Patent: Aug. 5, 2014

(54) INTEGRATED CONTOURED NEGATIVE PRESSURE BANDAGES

(75) Inventors: John A. Bennett, Villanova, PA (US); John-Yuhan Bai, San Gabriel, CA (US); Christopher A. Karbowski, Lancaster, PA (US)

(73) Assignee: Oakwell Distribution, Inc., King of Prussia, PA (US)

( * ) Notice: Subject to any disclaimer, the term of this patent is extended or adjusted under 35 U.S.C. 154(b) by 7 days.

(21) Appl. No.: 13/207,391

(22) Filed: Aug. 10, 2011

(65) Prior Publication Data

US 2012/0041403 A1    Feb. 16, 2012

Related U.S. Application Data

(60) Provisional application No. 61/373,233, filed on Aug. 12, 2010.

(51) Int. Cl.
*A61M 1/00* (2006.01)
*A61F 13/00* (2006.01)

(52) U.S. Cl.
CPC ... *A61F 13/00068* (2013.01); *A61F 2013/0054* (2013.01); *A61M 1/0088* (2013.01); *A61F 2013/00412* (2013.01); *A61F 2013/00536* (2013.01); *A61F 2013/00174* (2013.01)
USPC ...................................................... 604/319

(58) Field of Classification Search
USPC ........................................................ 604/319
See application file for complete search history.

(56) References Cited

U.S. PATENT DOCUMENTS

| 3,875,937 | A | * | 4/1975 | Schmitt et al. | 604/307 |
| 4,112,947 | A | * | 9/1978 | Nehring | 604/30 |
| 4,261,363 | A | * | 4/1981 | Russo | 604/174 |
| 4,573,965 | A | * | 3/1986 | Russo | 604/30 |
| 4,661,093 | A | * | 4/1987 | Beck et al. | 604/543 |
| 4,743,232 | A | * | 5/1988 | Kruger | 604/180 |
| 4,917,112 | A | * | 4/1990 | Kalt | 602/58 |
| 4,941,882 | A | * | 7/1990 | Ward et al. | 604/180 |
| 4,969,880 | A |   | 11/1990 | Zamierowski | |
| 5,106,362 | A | * | 4/1992 | Gilman | 602/47 |
| 5,261,893 | A | * | 11/1993 | Zamierowski | 604/180 |

(Continued)

OTHER PUBLICATIONS

Convatec USA Duaderm Signal Dressing, print of website for ConvaTec's Heel Bandage on Aug. 3, 2011.

(Continued)

*Primary Examiner* — Susan Su
*Assistant Examiner* — Guy K Townsend
(74) *Attorney, Agent, or Firm* — Miller Law Group, PLLC

(57) ABSTRACT

An integrated negative pressure bandage is constructed with a non-woven polyurethane matrix pad secured on the outside surface to a sheet of polyurethane film formed with an outer adhesive boundary to establish a seal against the skin of the patient around the wound site. The inner surface of the non-woven matrix pad is covered with a silver nitrate mesh to promote healing of the wound site when the bandage is placed on top of the wound. A drain tube is contained within the non-woven matrix pad for connection with a source of negative pressure to draw the fluids and exudates from the wound for removal to a canister that is located remotely from the bandage. Contoured versions of the integrated bandage are provided for use on portions of the human body that present difficult locations for applications of negative pressure therapy, including the toes, heel, limbs, and sacral region.

19 Claims, 13 Drawing Sheets

(56) References Cited

U.S. PATENT DOCUMENTS

| | | | |
|---|---|---|---|
| 5,636,643 A | 6/1997 | Argenta | |
| 5,645,081 A | 7/1997 | Argenta | |
| 5,678,564 A * | 10/1997 | Lawrence et al. | 600/574 |
| 5,685,859 A * | 11/1997 | Kornerup | 604/180 |
| 5,891,111 A * | 4/1999 | Ismael | 604/541 |
| 5,911,222 A * | 6/1999 | Lawrence et al. | 600/574 |
| 6,117,111 A * | 9/2000 | Fleischmann | 604/180 |
| 6,398,767 B1 * | 6/2002 | Fleischmann | 604/313 |
| 6,626,891 B2 * | 9/2003 | Ohmstede | 604/543 |
| 6,695,823 B1 * | 2/2004 | Lina et al. | 604/304 |
| 6,752,794 B2 * | 6/2004 | Lockwood et al. | 604/313 |
| 6,855,135 B2 * | 2/2005 | Lockwood et al. | 604/313 |
| 6,979,324 B2 * | 12/2005 | Bybordi et al. | 604/313 |
| 7,198,046 B1 * | 4/2007 | Argenta et al. | 128/897 |
| 7,216,651 B2 | 5/2007 | Argenta | |
| 7,361,184 B2 | 4/2008 | Joshi | |
| 7,381,859 B2 * | 6/2008 | Hunt et al. | 602/46 |
| 7,520,872 B2 * | 4/2009 | Biggie et al. | 604/319 |
| 7,524,315 B2 * | 4/2009 | Blott et al. | 604/543 |
| 7,615,036 B2 | 11/2009 | Joshi | |
| 2002/0032485 A1 * | 3/2002 | Flam et al. | 623/23.51 |
| 2002/0082567 A1 * | 6/2002 | Lockwood et al. | 604/307 |
| 2002/0115952 A1 * | 8/2002 | Johnson et al. | 602/41 |
| 2002/0161346 A1 * | 10/2002 | Lockwood et al. | 604/315 |
| 2004/0030304 A1 * | 2/2004 | Hunt et al. | 604/317 |
| 2007/0027414 A1 * | 2/2007 | Hoffman et al. | 602/2 |
| 2007/0066945 A1 * | 3/2007 | Martin | 604/313 |
| 2007/0083141 A1 * | 4/2007 | Flam et al. | 602/61 |
| 2007/0149912 A1 * | 6/2007 | Flam et al. | 602/61 |
| 2007/0219532 A1 * | 9/2007 | Karpowicz et al. | 604/540 |
| 2007/0293830 A1 * | 12/2007 | Martin | 604/289 |
| 2008/0108927 A1 * | 5/2008 | Sinyagin | 602/54 |
| 2008/0119773 A1 * | 5/2008 | Flick | 602/48 |
| 2008/0167593 A1 * | 7/2008 | Fleischmann | 602/48 |
| 2008/0243044 A1 * | 10/2008 | Hunt et al. | 602/58 |
| 2008/0286329 A1 * | 11/2008 | Campbell et al. | 424/423 |
| 2009/0280182 A1 * | 11/2009 | Beck et al. | 424/486 |
| 2009/0299251 A1 | 12/2009 | Buan | |
| 2010/0047324 A1 * | 2/2010 | Fritz et al. | 424/446 |

OTHER PUBLICATIONS

Convatec USA Duaderm Signal Dressing, print of website for ConvaTec's Oval Bandage on Aug. 3, 2011.

Convatec USA Duaderm Signal Dressing, print of website for ConvaTec's Sacral Bandage on Aug. 3, 2011.

Kalypto Negative Pressure Foot Bandage, print of instruction manual from web site on Aug. 3, 2011.

Kalypto Negative Pressure Oval Bandage, print of instruction manual from web site on Aug. 3, 2011.

Kalypto Negative Pressure Sacral Bandage, print of instruction manual from web site on Aug. 3, 2011.

Mepilex Heel Bandage, print of web site for Miplex Wound Care on Aug. 3, 2011.

Mepilex Border Sacral Bandage, print of web site for Miplex Wound Care on Aug. 3, 2011.

\* cited by examiner

Fig. 1
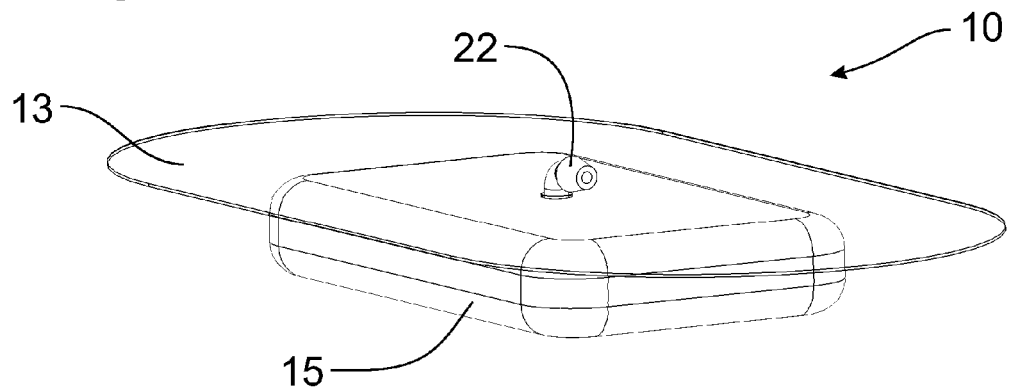
Fig. 2
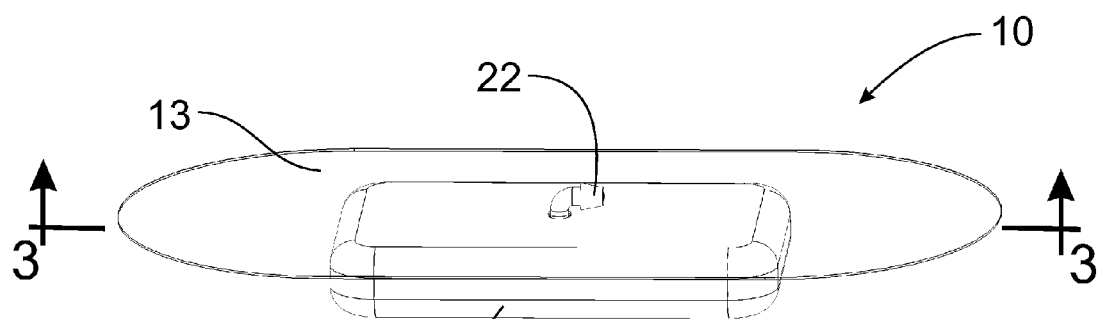
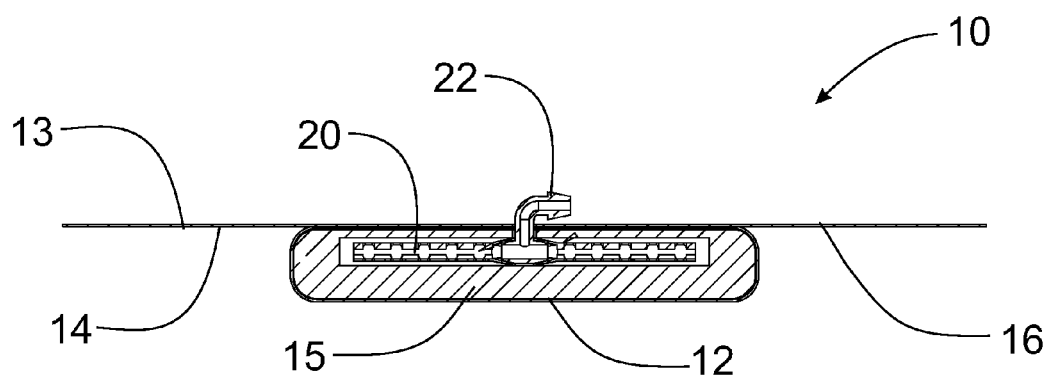
Fig. 3

Fig. 4
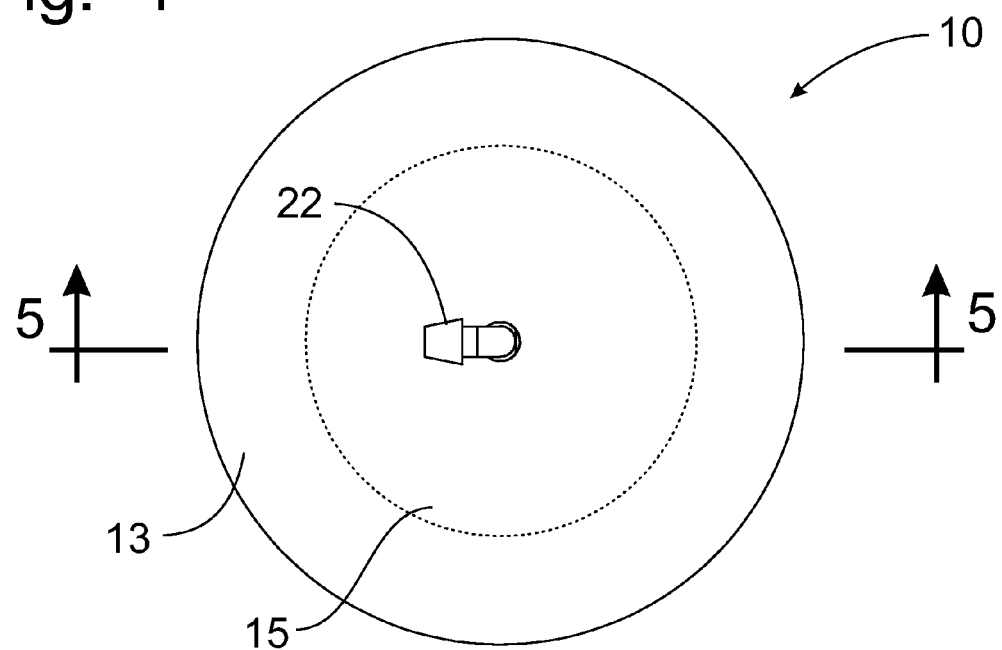
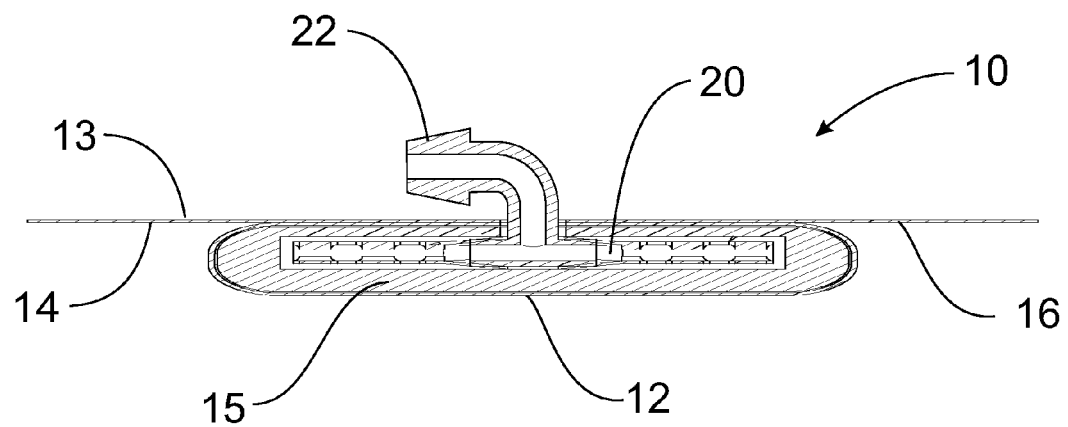
Fig. 5

Fig. 7
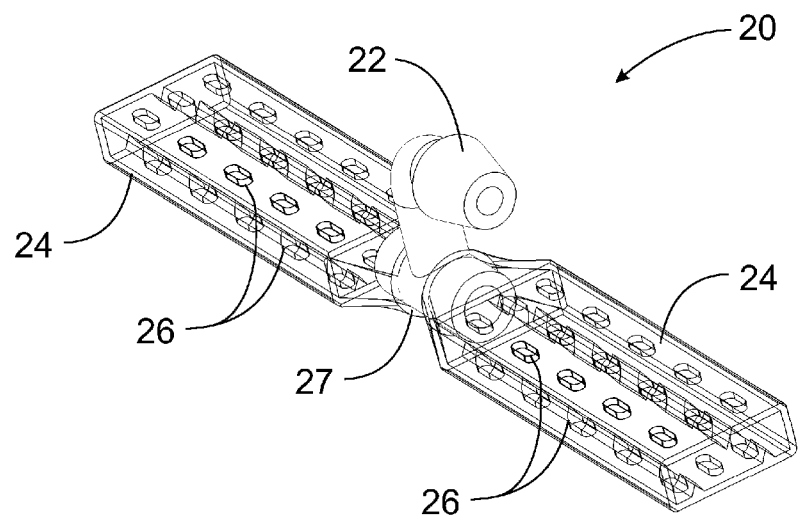
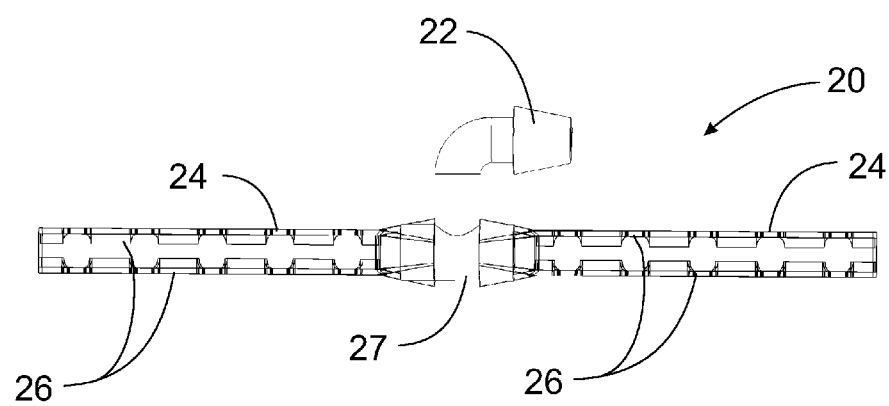
Fig. 8

Fig. 11
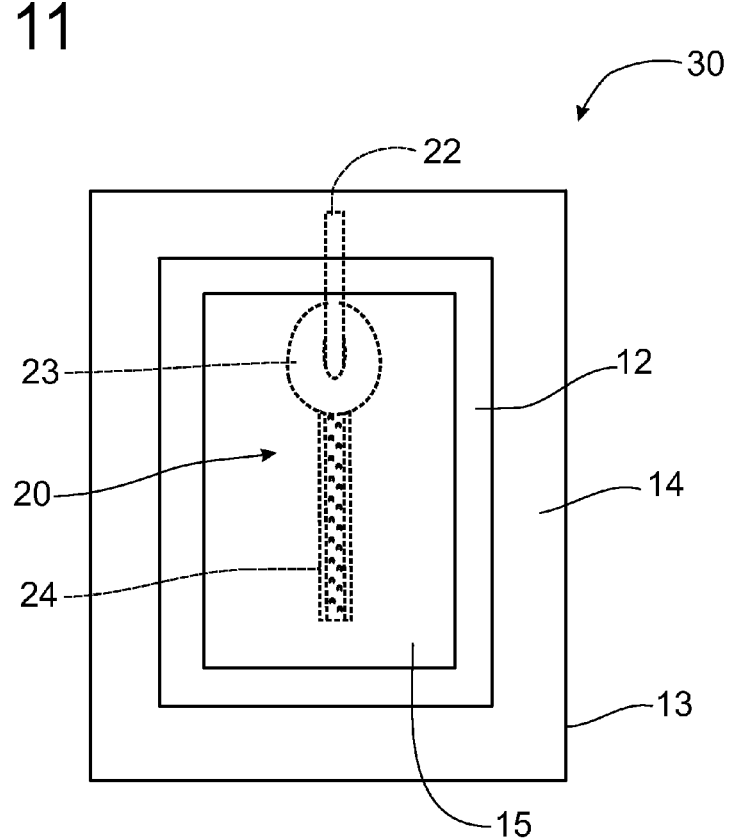
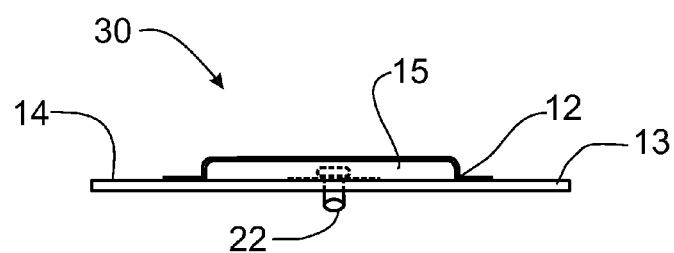
Fig. 12

Fig. 13
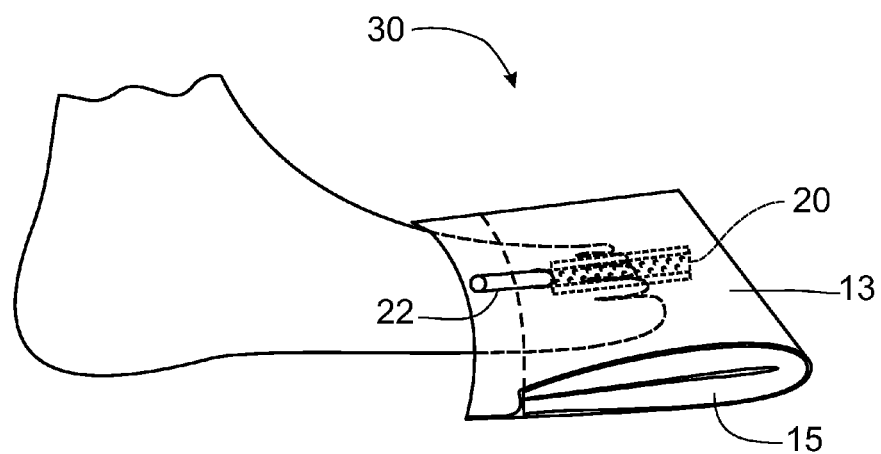
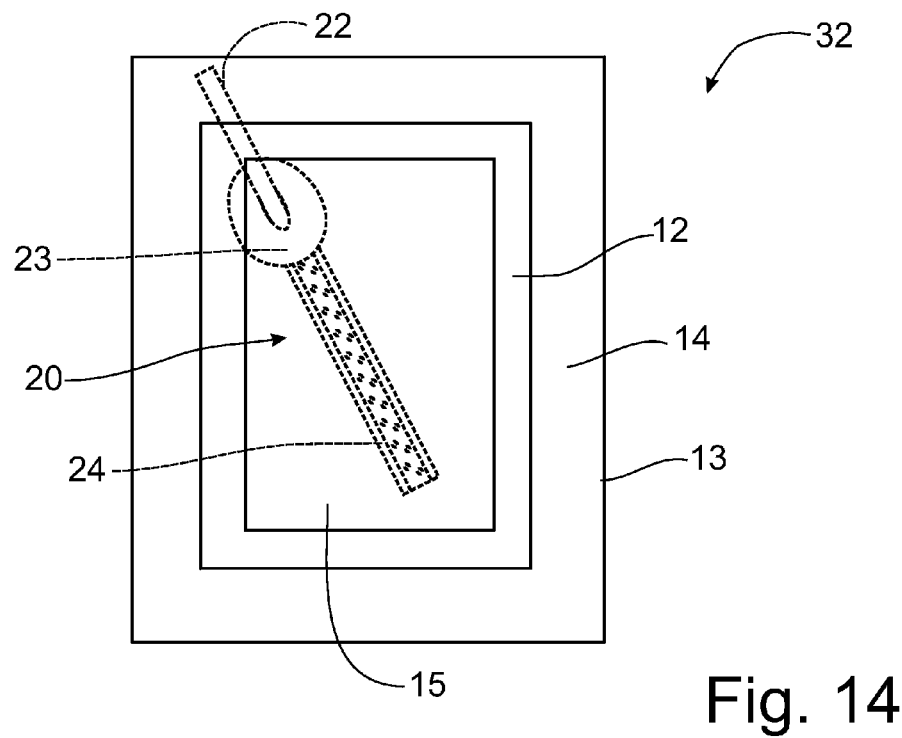
Fig. 14

Fig. 15
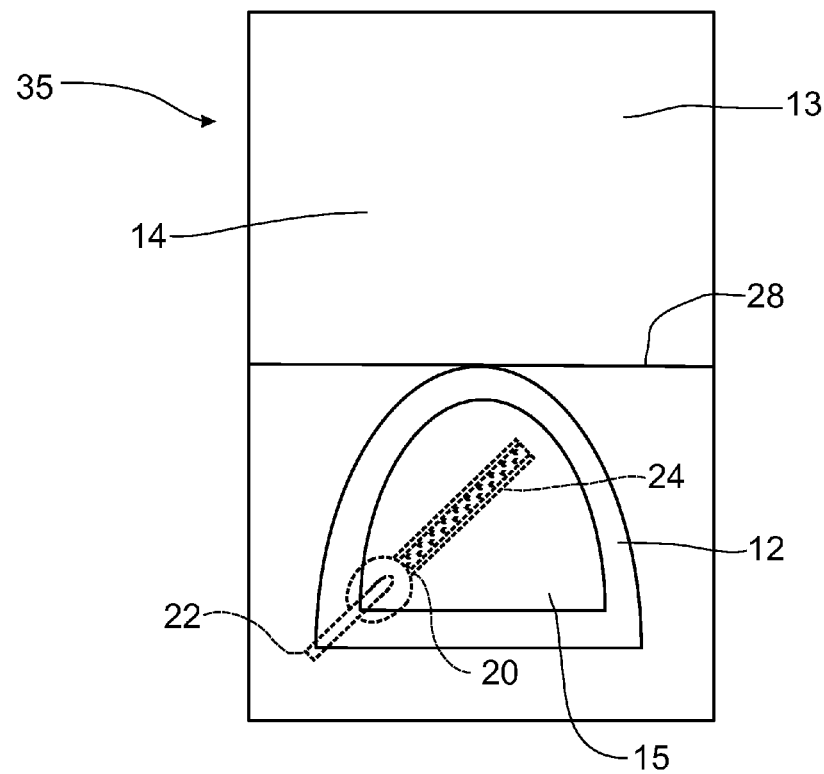
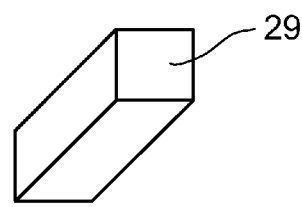
Fig. 16

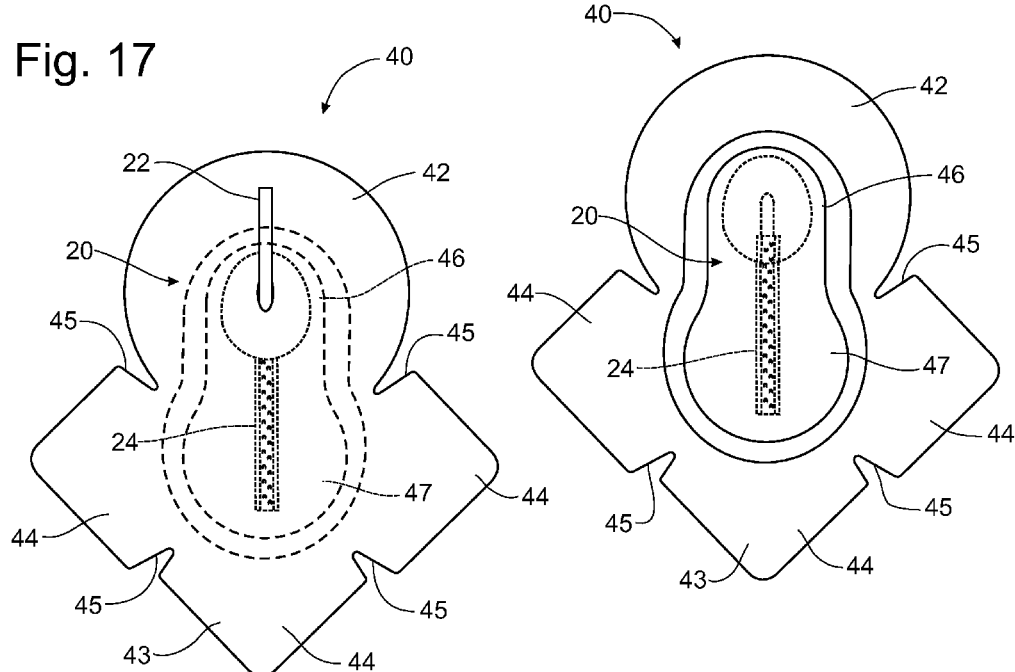

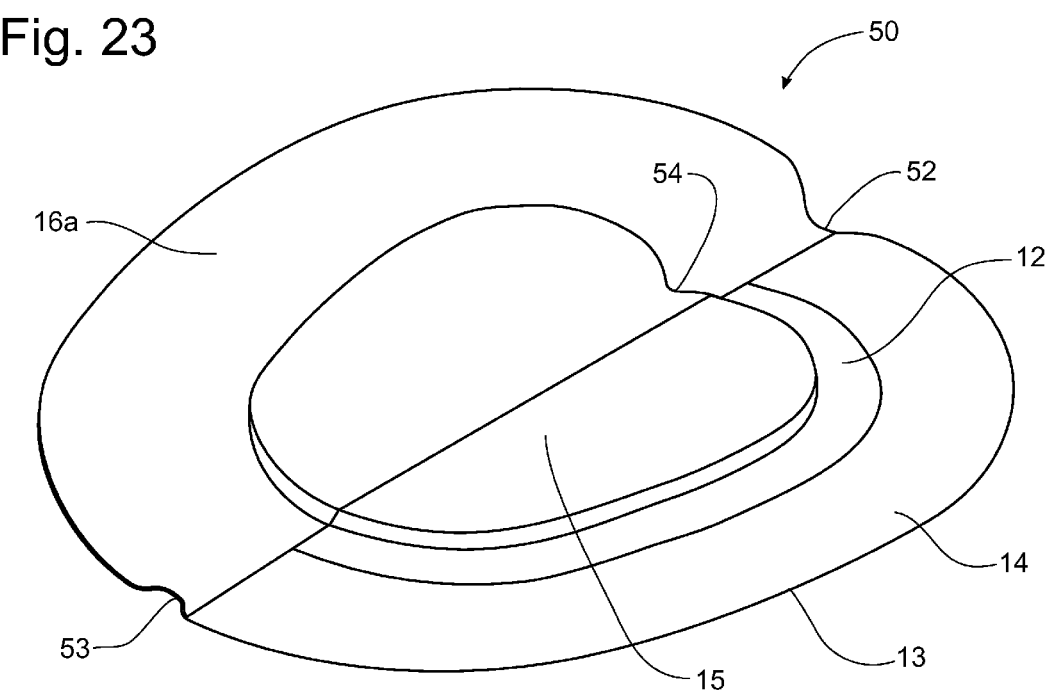

INTEGRATED CONTOURED NEGATIVE PRESSURE BANDAGES

CROSS-REFERENCE TO RELATED APPLICATIONS

This application claims domestic priority on U.S. Provisional Patent Application Ser. No. 61/373,233, filed on Aug. 12, 2010, the content of which is incorporated herein by reference in it entirety.

FIELD OF THE INVENTION

The present invention relates generally to negative pressure bandages operable to remove exudates and fluids from a wound and, more particularly, to a bandage structure that is specifically contoured to fit body parts that present difficulties in affixing and applying negative pressure bandages.

BACKGROUND OF THE INVENTION

Negative pressure therapy has been utilized for the treatment of a variety of wounds by medical practitioners. Conventional negative pressure bandages are generally large in size and often require the use of complicated equipment such as suction pumps, vacuum pumps and complex electronic controllers to apply a negative pressure within the bandage to draw exudates and fluids away from the wound to a remote collection container. Typically, negative pressure therapy involves other associated equipment, such as the exudates/fluid collection canisters, liquid transporting conduits, and pressure regulators/transducers/sensors. As a result, negative pressure bandages and related equipment tends to be bulky and relatively costly. Such complexity typically requires professional placement of the bandage and connection to the pump and collection canister, followed by consistent, regular patient supervision and monitoring. Generally, negative pressure bandages are applied for approximately two days, at which time the bandage must be removed and replaced by professional technicians.

The rising costs of healthcare and of medical devices, such as negative pressure bandages, provide incentive to develop less expensive equipment, and procedures that are more easily utilized to reduce the costs associated with the use of negative pressure therapy while improving on the effectiveness of the therapy. Simplification of the procedures and the equipment can allow in-home use of such therapies with a minimum of professional supervision and monitoring of the patients. Furthermore, patients continue to demand devices that are more easily portable to allow travel and mobility while utilizing the therapy.

Conventional applications of negative pressure therapy to wound sites typically incurs the cutting of a porous foam pad to fit into the wound, followed by an application of an adhesive surgical drape over the pad and wound site to seal against the skin of the patient around the wound site. The fluids and exudates from the wound can be removed from the bandage to a remote location through an application of a vacuum to a connector fitted into the adhesive surgical drape, such as is shown in U.S. Pat. No. 5,636,643, granted on Jun. 10, 1997, in U.S. Pat. No. 5,645,081, granted on Jul. 8, 1997, and in U.S. Pat. No. 7,216,651, granted on May 15, 2007, all of which were issued to Louis Argenta. Alternatively, the foam pad can be utilized as a storage reservoir by incorporating a hydrophobic filter at the connector to prevent the fluids from leaving the bandage, as is reflected below in greater detail. Negative pressure therapy is provided commercially by at least KCI, Smith & Nephew, Kalypto, Medela, Mepilex and Convatec. An earlier negative pressure wound therapy embodiment is disclosed in U.S. Pat. No. 4,969,880, issued to David S. Zamierowski on Nov. 13, 1990.

The application of conventional negative pressure bandages to certain parts of the body presents substantial difficulties in maintaining a seal against the skin around the wound. Without the negative pressure bandage being sealed against the skin of the patient, the negative pressure system will not operate. Certain body parts, such as heels, ankles and toes present a multi-faceted skin surface against which the negative pressure bandage must seal. Conventional practices with the negative pressure bandages, such as are described below, require the planar bandages to be cut, shaped and compromised with respect to the sealing portion of the bandage to fit against the contoured body part.

In U.S. Pat. No. 7,615,036, granted to Ashok Joshi, et al on Nov. 10, 2009, a negative pressure bandage is disclosed in which the bandage has a housing that is sealed to the body surface of the patient and defines a liquid retention chamber coupled to a vacuum source to apply a negative pressure on the liquid retention chamber so that the exudates and fluids are drawn into an absorptive material within the liquid retention chamber. This liquid retention chamber is located adjacent to the wound from which the exudates and fluids are removed.

Improvements to negative pressure wound therapy devices can be found in U.S. Patent Publication No. 2009/0299251 of John Buan published on Dec. 3, 2009, to enhance the sealing of the bandage to the body surface of the patient. In this negative pressure wound therapy device, a vacuum is applied to a collection chamber in which an absorptive pad is disposed to collect the exudates and fluids drawn away from the wound by the vacuum (negative pressure). To enhance the connection of the tubing extending between the vacuum pump and the negative pressure therapy device, an extended length connector is disclosed, which will accommodate connection when ace wrap or other coverings are applied to the exterior of the bandage.

In U.S. Pat. No. 7,361,184, granted on Apr. 22, 2008, to Ashok Joshi, an attempt to provide a self-contained negative pressure wound therapy device is provided so that the device does not require connection to a remote vacuum source. In this negative pressure wound dressing, an absorptive pad is also disposed in the fluid collection chamber, which is located adjacent to the wound, the negative pressure drawing the exudates and fluids away from the wound into the absorptive pad. Several early embodiments of negative pressure bandages can be found in U.S. Pat. No. 5,636,643, granted to Louis Argenta, et al on Jun. 10, 1997, all of which, however, utilize a single chamber configuration in which a vacuum is applied to the fluid collection chamber and the exudates and fluid is drawn away through tubing to a remote pump and fluid retention chamber.

It would be desirable to provide a contoured negative pressure bandage that will be adapted to be affixed to a specific contoured body part to remove exudates and fluid from a wound located on that contoured body part.

SUMMARY OF THE INVENTION

It is an object of this invention to overcome the disadvantages of the prior art by providing an integrated negative pressure wound therapy bandage.

It is another object of this invention to provide negative pressure wound therapy bandages that are contoured to fit specific areas of a patient's body that are conventionally difficult to provide a seal for use in negative pressure wound therapy.

It is a feature of this invention that a negative pressure bandage is integrated into a single applicable bandage that can provide negative pressure wound therapy.

It is an advantage of this invention that the components parts of the negative pressure bandage do not require individual installation on a patient to provide negative pressure wound therapy.

It is another advantage of this invention that the integrated bandage is not inserted into the surface of the wound, but is positioned over top of the wound, to provide negative pressure wound therapy.

It is another feature of this invention that the integrated bandage structure provides a non-woven polyurethane matrix mesh impregnated with silver nitrate to overlie the wound being treated.

It is still another advantage of this invention that the silver nitrate mesh inhibits infection and promotes healing of the wound.

It is yet another feature of this invention that the integrated bandage structure also includes a drain tube disposed within the non-woven polyurethane matrix for connection to a source of negative pressure to withdraw the exudates and fluids from the wound to a remote canister for collection thereof.

It is yet another advantage of this invention that the non-woven matrix does not absorb the fluids and exudates, but allows the collection thereof into the drain tube for removal from the bandage and from the wound site.

It is still another object of this invention to provide a therapy for wounds to keep the wound clear of excessive moisture and exudates, and to promote healing of the wound.

It is yet another object of this invention to provide an integrated negative pressure bandage that is configured to fit onto portions of the human body that is difficult to attach a negative pressure bandage.

It is an advantage of this invention that the contoured negative pressure bandages are configured to provide a seal around a wound found on certain difficult to fit portions of the human body.

It is still another object of this invention to provide negative pressure bandages that are contoured to fit on the foot, at both the toe and heel portions of the foot, on limbs, and on the sacral region of the human body and provide a seal against the skin around the wound so that negative pressure therapy can be provided to the wound site.

It is yet another advantage of this invention that the time to apply a negative pressure bandage to a wound site is reduced by the utilization of an integrated bandage that allows the wound fluids and exudates to be withdrawn from the bandage to a remote canister.

It is a further feature of this invention that the contoured negative pressure bandage for application to the heel of a patient's foot is formed with junctions, such as cutouts, to facilitate the sealing of the bandage around the heel.

It is still a further feature of this invention that the drain tube and associated connector can be oriented diagonally to the primary axes of the bandage to position the connector for attaching the vacuum source to the drain tube in an easily accessible and unobtrusive location.

It is yet another object of this invention to provide an integrated negative pressure bandage that is durable in construction, inexpensive of manufacture, facile in assemblage, and simple and effective in use.

It is a further object of this invention to provide a negative pressure bandage that is contoured to fit portions of the human body that are difficult to apply negative pressure wound therapy to establish an integrated negative pressure bandage that is simple and effective in use.

These and other objects, features and advantages are accomplished according to the instant invention by providing an integrated negative pressure bandage having a non-woven polyurethane matrix pad secured on the outside surface to a sheet of polyurethane film formed with an outer adhesive boundary to establish a seal against the skin of the patient around the wound site. The inner surface of the non-woven matrix pad is covered with a silver nitrate mesh to promote healing of the wound site when the bandage is placed on top of the wound. A drain tube is contained within the non-woven matrix pad for connection with a source of negative pressure to draw the fluids and exudates from the wound for removal to a canister that is located remotely from the bandage. Contoured versions of the integrated bandage are provided for use on portions of the human body that present difficult locations for applications of negative pressure therapy, including the toes, heel, limbs, and sacral region.

BRIEF DESCRIPTION OF THE DRAWINGS

The foregoing and other objects, features, and advantages of the invention will appear more fully hereinafter from a consideration of the detailed description that follows, in conjunction with the accompanying sheets of drawings. It is to be expressly understood, however, that the drawings are for illustrative purposes and are not to be construed as defining the limits of the invention.

FIG. 1 is a perspective view of an integrated negative pressure bandage incorporating the principles of the instant invention, the bandage of FIG. 1 being shaped for utilization for injuries or wounds to generally planar portions of the body;

FIG. 2 is a side perspective view of the integrated negative pressure bandage shown in FIG. 1;

FIG. 3 is a cross-sectional view of the integrated negative pressure bandage corresponding to lines 3-3 of FIG. 2;

FIG. 4 is a top plan view of an integrated bandage similar to that of FIG. 1, but having a circular shape;

FIG. 5 is a cross-sectional view of the integrated bandage corresponding to lines 5-5 of FIG. 4;

FIG. 7 is an upper perspective view of a first embodiment of a drain tube and connector utilized in the planar bandage shown in FIG. 1;

FIG. 8 is a side elevational view of the drain tube and connector shown in FIG. 7.

FIG. 11 is a top plan view of a first embodiment of a contoured negative pressure bandage incorporating the principles of the instant invention for a patient's foot, shown in an opened configuration in which the bandage would be shipped to the patient, the release members not being shown for purposes of clarity;

FIG. 12 is a side elevational view of the contoured negative pressure bandage for a foot as shown in FIG. 11, the release members not being shown for purposes of clarity;

FIG. 13 is a perspective view of the contoured negative pressure bandage as shown in FIG. 11 folded over the toes on the foot of a representative patient;

FIG. 14 is a top plan view of a second embodiment of the contoured negative pressure bandage for a patient's foot, the release members not being shown for purposes of clarity;

FIG. 15 is a top plan view of a third embodiment of the contoured negative pressure bandage for a foot, the bandage being shown in an unfolded configuration corresponding to the configuration in which the bandage would be shipped to the patient for subsequent use, the release members not being shown for purposes of clarity;

FIG. 16 is a perspective view of a wedge member for use in conjunction with the contoured negative pressure bandage shown in FIGS. 12-16;

FIG. 17 is a top plan view of a contoured negative pressure bandage for use with a patient's heel;

FIG. 18 is a bottom plan view of the contoured negative pressure bandage for heels as shown in FIG. 17, the release members not being shown for purposes of clarity;

FIG. 23 is a perspective view of the contoured negative pressure bandage shown in FIG. 22.

DETAILED DESCRIPTION OF THE PREFERRED EMBODIMENT

Figure 6:
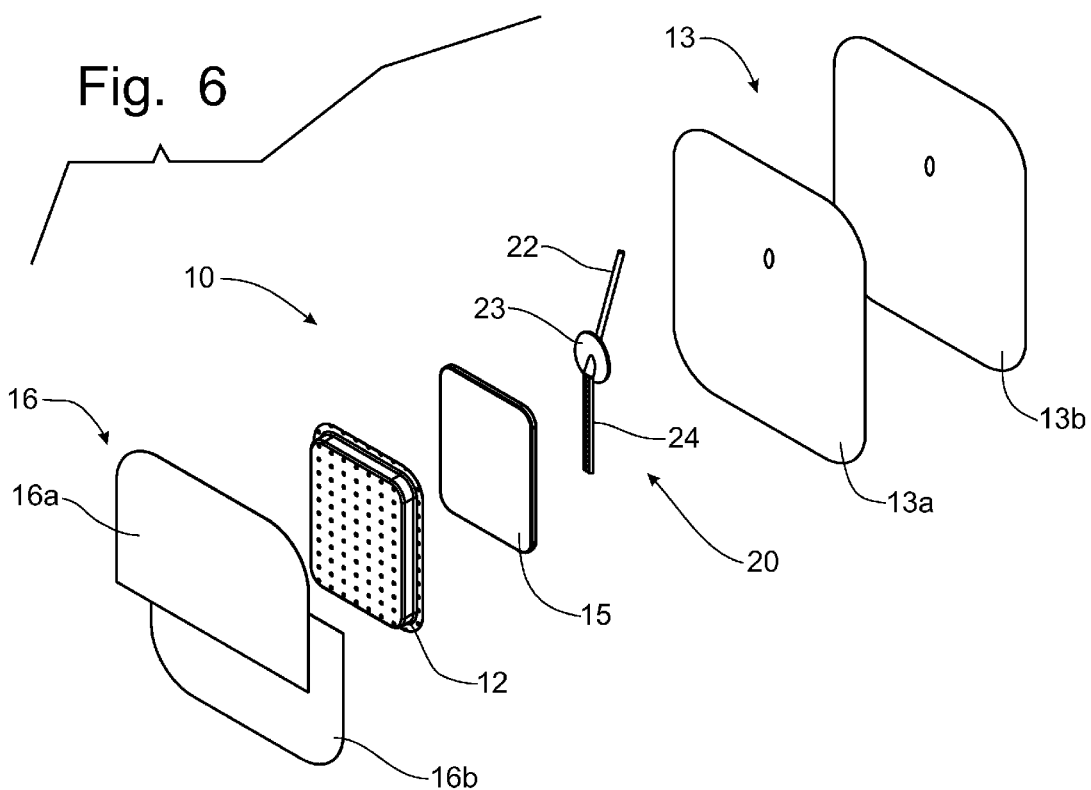
FIG. 6 is an exploded view of a different embodiment of the integrated negative pressure bandage similar to that shown in FIGS. 1 and 4.

Referring to the FIGS. 1-6, integrated negative pressure bandages incorporating the principles of the instant invention can best be seen. One of ordinary skill in the art will recognize that the scale of the components of the negative pressure bandages is exaggerated to shown the details of the components. For example, the wound contact member depicted in each of the drawings is enlarged to shown the configuration thereof. The thicknesses and relative sizes of other components may also be distorted to show the invention. Specific contoured configurations of the integrated negative pressure bandages are depicted in FIGS. 12-23.

The different embodiments of the contoured negative pressure bandages shown in the drawings have some common features relating to the formation of the integrated negative pressure bandage. Each of the bandages have an outer shaped cover formed from a liquid impermeable material, such as polyurethane film, that can be formed into the specific shape required for the bandage configuration, yet provide sufficient flexibility to allow attachment of the bandage to the skin surrounding the injury being treated. The outer cover is provided with an area of adhesive around a perimeter portion of the bandage where the cover would be engaged with the skin around the wound being treated to create a seal between the perimeter of the bandage and the skin. A protective release film would be applied to the adhesive portion until the bandage is to be applied to a patient, substantially covering the entire inner surface of the bandage.

Furthermore, each of the bandages will have a wound contact member secured to the outer film cover to be positioned between the cover and the body part being treated. While this wound contact member can be formed from gauze padding covered by a mesh layer, preferably a polyethylene mesh impregnated with silver nitrate, the wound contact member is preferably formed with a permeable polymer matrix layer, more specifically a non-woven polyurethane matrix pad is preferred, that will allow the passage of liquids through the pad to keep the surface of the wound contact member against the wound site as dry as possible. Within this wound contact padding is a drain tube connected to an external connector to apply a negative pressure to the bandage that will draw the fluids and exudates from the wound being treated. The surface of the wound contact member, which is in direct contact with the wound being treated, is provided with a mesh layer, preferably a polyethylene mesh impregnated with silver nitrate, to protect the wound and promote healing. In operation, the negative pressure bandage keeps the wound dry and does not allow the fluid to accumulate within the bandage, thus keeping the bandage from bulking up with accumulated fluids that can disrupt the seal around the perimeter of the bandage.

Referring now to FIGS. 1-6, an integrated negative pressure bandage 10 incorporating the principles of the instant invention can best be seen. The bandage 10 is formed with a non-woven polymer matrix pad 15 covered on an inside surface by a polyethylene mesh layer 12 that serves as a wicking function to draw fluids into the pad 15 and keeps the pad 15 from engaging the surface of the wound when the bandage 10 is applied. Preferably, the mesh layer incorporates a coating of, or is impregnated with, a compound of silver nitrate to promote healing and inhibit infection. The outer surface of the non-woven polymer pad 15 is attached to a polyurethane film 13 formed with an adhesive covered perimeter portion 14. A drain tube 20 is positioned within the pad 15 and exits the bandage 10 through an opening within the polyurethane film 13 to terminate in a connector 22 adapted for connection to a conduit leading to a vacuum source (not shown) and an associated canister reservoir (not shown). A seal pad 23 can be provided at the opening through the polyurethane film 13 for engagement with the connector 22 to enhance the seal of the bandage 10 when applied to a patient.

Preferably, the polyurethane film 13 can be formed with an inner transparent film member 13a and an outer opaque, or skin colored, film member 13b. The adhesive-covered surface of the polyurethane film member 13a is preferably covered by a release member 16 that is removed from the bandage 10 when the bandage is to be applied to the patient to expose the adhesive boundary 14 for attachment to the patient's skin around the wound site. More preferably, the release member 16 covers the entire inside surface of the bandage 10 before being removed and can be formed as overlapping members 16a and 16b. The outer film member 13b is preferably constructed from non-woven polyurethane to provide a covering that has a look somewhat like human skin.

The general configuration of the drain tube 20 and connector 22 utilized in each of the bandages described above and below, is shown generically in FIGS. 7-10. One skilled in the art will recognize that the drain tube 20 can be shaped specifically to conform to any particular shape or configuration of the bandage 10; however, FIGS. 7-10 depict the drain tube 20 as having a linear configuration. One skilled in the art will also understand that the length and width of the drain tube 20 is also dependent on the size and shape of the specific bandage 10. The connector 22 is of a conventional size and shape for connection to tubing that would interconnect the connector 22 with a vacuum pump (not shown).

The drain tube 20 in the first embodiment depicted in FIGS. 7 and 8 is formed from a pair of opposing, relatively flat body fluid collection members 24 that are formed with slotted openings 26 in the top and bottom surfaces thereof to collect fluids and exudates from the wound through the wound contact member 15. The opposing fluid collection members 24 are connected to a central collector member 27 that forms a "T" connection with the external connector 22 so that the negative pressure applied to the connector 22 extracts the fluids and exudates from the fluid collection members 24 through the central collector member 27 and out through the connector 22 to an storage device (not shown).

Figure 9:
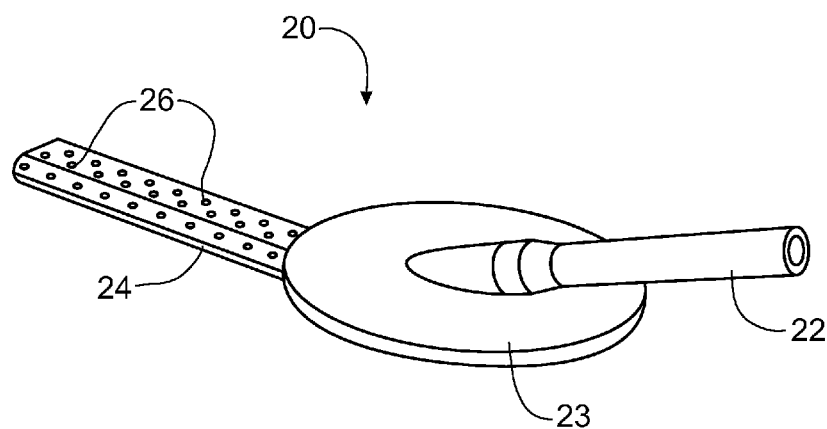
FIG. 9 is an upper perspective view of an alternate embodiment of a drain tube as shown in FIG. 7.
Figure 10:
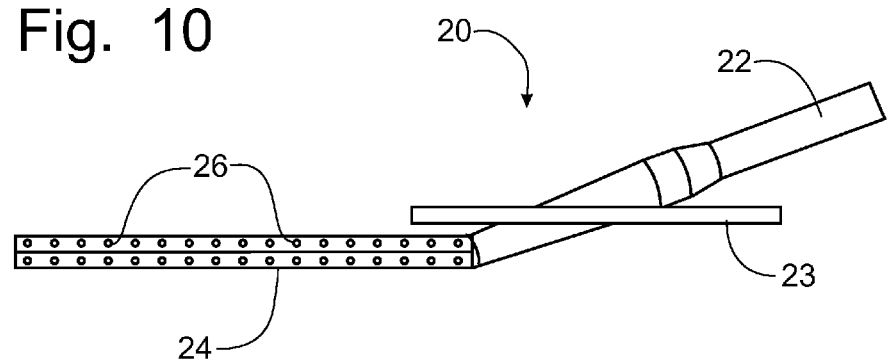
FIG. 10 is a side elevational view of the drain tube shown in FIG. 9.
Figure 19:
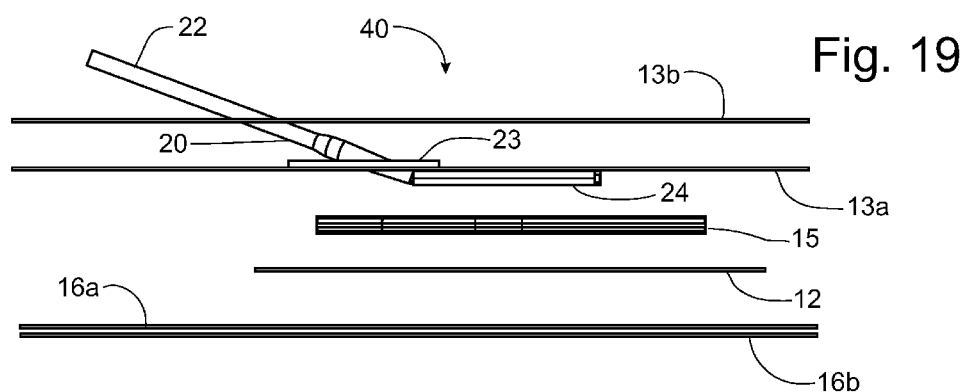
FIG. 19 is an exploded view of the contoured negative pressure bandage for heels as shown in FIG. 17.
Figure 20:
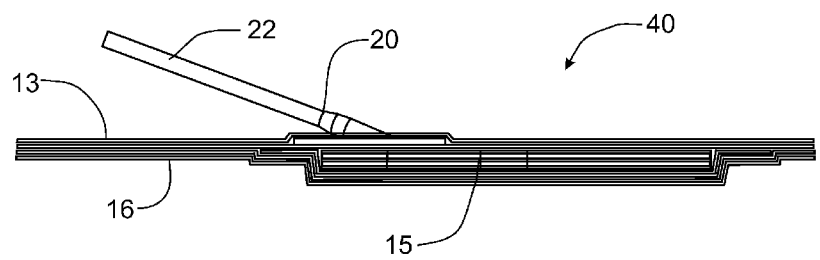
FIG. 20 is a side elevational view of the contoured negative pressure bandage for heels.

A second embodiment of the drain tube 20 is depicted in FIGS. 9 and 10 as a single tube configuration. The single flat body fluid collection member 24 is connected at one end thereof to the connector 22 which can pass through the seal pad 23, and also through the polyurethane film 13, for connection with the vacuum source (not shown). As depicted in the embodiment of FIGS. 7 and 8, the flat fluid collection member 24 is formed with openings 26 in the top and bottom surfaces. As depicted in FIGS. 8 and 10, the sides of the fluid collection member 24 can also be formed with openings 26 and those openings 26 can be in any shape from oval to circular, or other geometric shapes.

A first embodiment of a contoured integrated negative pressure bandage 30 is shown in FIGS. 11-13, configured for use with the patient's toes. As with the integrated bandage described above with respect to FIGS. 1-6, this contoured bandage 30 is formed with an outer polyurethane film cover 13 formed with an outer adhesive boundary 14 located to the exterior of the mesh 12 which covers the non-woven polymer matrix pad 15. In this embodiment of the contoured bandage 30, the drain tube 20 is positioned at one end of the pad 15 such that the fluid collection member 24 extends substantially to the opposing end of the pad 15. In FIG. 14, a second embodiment of the foot bandage 32 is shown in which the drain tube 20 is oriented diagonally across the pad 15 such that the connector 22 is positioned to one side of the bandage 30.

In the application of this first embodiment of the contoured bandage 30, as is depicted schematically in FIG. 13, the bandage 30 is wrapped around the ends of the patient's toes in a manner where the pad 15 is located both above the patient's foot and below the patient's foot. The drain tube 20 is sufficiently flexible to allow the associated bend in the bandage 30 such that the fluid collection member 24 is also located above and below the patient's foot. The connector 22 is oriented over the top of the foot for connection to the vacuum pump (not shown). When the second embodiment of the bandage 32 is applied, the connector 22 is located at the top of the patient's foot, but to one side of the foot.

Yet a third embodiment of the contoured negative pressure bandage 35 configured for application to a patient's foot is shown in FIG. 15. The non-woven polymer matrix pad 15 is formed smaller than the first embodiment shown in FIGS. 11 and 14, and preferably in a semi-circular shape. The pad 15 is located at one end of the polyurethane film cover 13, terminating at a center fold line 28 so that the opposing half of the film cover 13 is devoid of a pad 15. Furthermore, most of the opposing half of the film cover 13 can be covered with a layer of adhesive 14. In application, the third embodiment of the foot bandage 35 is applied so that the pad 15 covers the open wound.

If the wound is on the bottom of the patient's foot, then the opposing half of the film cover 13 is wrapped over the ends of the toes and sealed against the top of the foot. Since the drain tube 20 is oriented diagonally, the connector 22 will project from one side of the bandage 35 to be connected to the vacuum pump (not shown). The ends of the patient's toes should be positioned proximate to the middle of the pad 15 so that the fold line 28 is spaced from the ends of the patient's toes. The adhesive areas 14 on the opposing side of the film cover 13 and around the pad 15 and seal against each other and against the patient's foot to provide a seal around the pad 15 for the application of negative pressure therapy.

In FIG. 16, a wedge member 29 is schematically shown. Preferably, for ease of manufacture, the wedge member 29 is rectangular in shape, but could be formed in a triangular or wedge shape as well. The purpose of the wedge member 29 is to separate the patient's toes prior to application of the bandage 30, 32 or 25 to the patient's foot. Often the open would on a patient's foot, whether on top or on the bottom of the foot, will extend between the patient's toes. Separating the toes adjacent the open wound with a wedge member 29 will increase the effectiveness of the negative pressure therapy.

Figure 21:
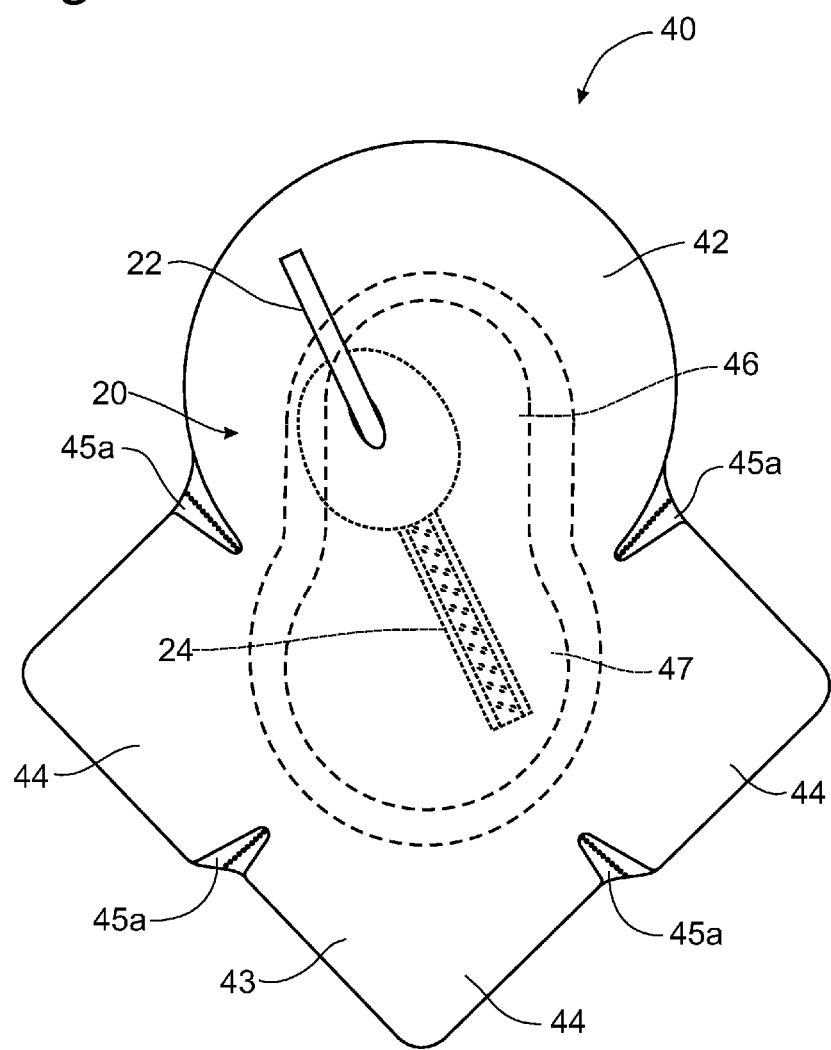
FIG. 21 is a top plan view of an alternative embodiment of the contoured negative pressure bandage for heels, similar to that shown in FIG. 17.

Referring now to FIGS. 17-21, an integrated bandage 40 contoured for application to a patient's heel is shown. As with the bandages described above, the heel bandage 40 has a shaped polyurethane film cover 13 on the outside surface of a non-woven polymer matrix pad 15 that has a silver nitrate mesh 12 on the inside surface. The polyurethane film cover 13 has a particular shape configured to be applied to the patient's heel. The film cover 13 has an upper rounded portion 42 surrounding an upper portion 46 of the pad 15 where the connector 22 is located. The lower portion 43 of the film cover 13 is formed with three flaps 44 projecting outwardly from the lower portion 47 of the pad 15. The flaps 44 are separated by junctions 45 that provide flexibility in the application of the adhesive covered flaps 44 to the patient's skin. The junctions 45 between the flaps 44 can be formed as cutouts 45, as is shown in FIGS. 17 and 18, or as a web 45a, as is depicted in FIG. 21. The drain tube 20 in the first embodiment of the heel bandage 40 is oriented along the major vertical axis of the bandage 40.

In application, the heel bandage 40 is positioned so that the lower portion 47 covers the open wound and the fluids and exudates can be evacuated from the wound via the drain tube 20. The rounded upper portion of the film cover 13 is easily applied to the lower part of the patient's calf irrespective of the orientation of the heel bandage 40 to the patient. The lower portion 43 of the film cover 13, however, is typically applied to the patient's ankle, which is much more difficult to obtain a seal. The junctions 45 between the flaps 44 allow the flaps 44 to be oriented as needed to obtain a seal against the patient's ankle area. Furthermore, the junctions 45 provide a place where the medical service provider can tear the film cover 13 if further modifications become necessary. In FIG. 21, a second embodiment of the heel bandage 49 is depicted. The component parts are formed as described above, except for the orientation of the drain tube 20, which is positioned diagonally across the pad 15 so that the connector 22 exits the polyurethane film cover member 13 at one side thereof. Furthermore, the junctions are depicted as perforated webs 45a between the flaps 44 to allow selective tearing of the webs 45a to accomplish the folding of the flaps 44 and the sealing of the bandage 10.

For wounds on the bottom of the heel, the heel bandage 40 is applied with the lower portion 47 of the pad 15 located under the foot against the open wound. The upper portion of the film cover 13 can be secured against the back portion of the patient's leg and the flaps 44 can be wrapped around the sides of the foot and along the sole. The connector 22 will be oriented vertically in back of the leg. If the wound is in the rear part of the heel, the lower part 47 of the pad 15 is positioned over the wound while the flaps 44 are wrapped around the sides of the ankle and underneath the heel. If the wound is on the ankle along the side of the foot, the lower part 47 of the pad 15 is placed over the wound with the upper portion 42 of the film cover 13 being oriented along the side of the leg. The flaps 44 can then be secured to the inside of the foot, behind the heel, and underneath the foot. The junctions 45 in each of the scenarios noted above enable the three respective flaps 44 to be secured against the patient's foot in different planes and in different orientations.

Figure 22:
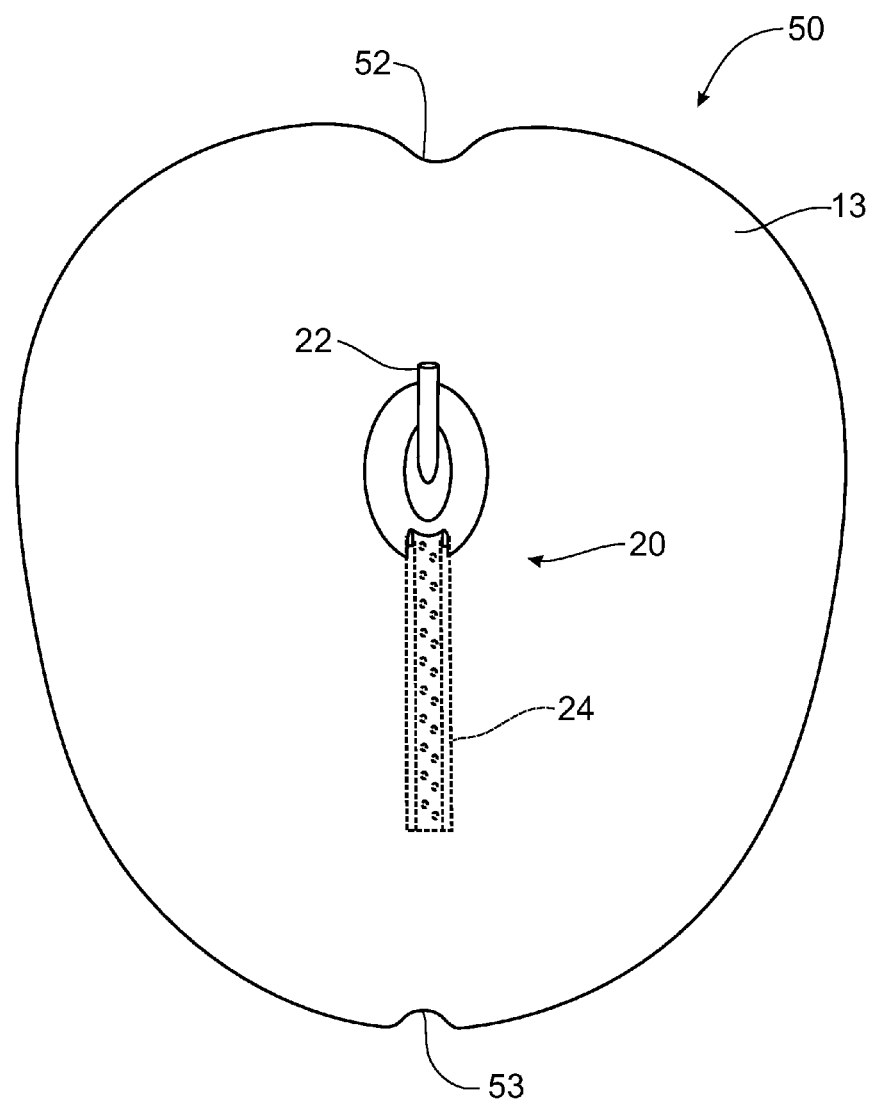
FIG. 22 is a top plan view of the contoured negative pressure bandage for use on the sacral region of a patient.

An integrated negative pressure bandage 50 contoured to be applied to the sacral region of the patient is shown in FIGS. 22 and 23. As described above, the sacral bandage 50 is formed with a non-woven polymer matrix pad 15 having affixed to the outside surface thereof a polyurethane film cover 13 and to the inner surface thereof a mesh 12 impregnated with silver nitrate. The drain tube 20 terminates in a connector 22 above the film cover 13 and includes a fluid collection member 24 embedded into the pad 15. The bandage 50 is formed with a curved indent 52, 53 at the top and at the bottom, respectively, to conform to the shape of the sacral region of the patient. Similarly, the pad 15 is formed with a curved indent 54 at the top central portion thereof.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiments of the invention; however, concepts, as based upon the description, may be employed in other embodiments without departing from the scope of the invention. The invention is not otherwise limited, except for the recitation of the claims set forth below.

Having thus described the invention, what is claimed is:

1. An integrated negative pressure bandage for removing fluid and exudates from a wound on a patient, comprising:
   a non-woven polymer matrix pad having an upper surface and a lower surface;
   a polymer film cover integrally affixed to said upper surface of said pad before being applied to said wound, said film cover having a peripheral boundary surrounding said pad, said peripheral boundary including an adhesive layer mounted thereon;
   a connection port incorporated into said film cover to be in flow communication with said pad;
   a mesh layer covering said lower surface of said pad and being integrally secured to said film cover;
   a drain tube embedded into said upper surface of said pad below said film cover to be integrally incorporated into said bandage, said drain tube having a fluid collection member formed with a plurality of openings therein and being in flow communication with said pad, said drain tube being connected to said connection port for attachment to a remote vacuum pump to remove fluids and exudates from said wound through said pad; and
   a release member removably attached to said adhesive layer and covering said adhesive layer and said pad, said release member being an integral part of said bandage before being removed from said adhesive layer to expose said adhesive layer for utilization.

2. The integrated negative pressure bandage of claim 1 wherein said polymer film cover is formed with an inner layer and an outer layer, said outer layer being opaque.

3. The integrated negative pressure bandage of claim 1 wherein said film cover has an opening therethrough for the passage of said connector of said drain tube, said drain tube further including a seal pad reinforcing said film cover around said opening and sealing the passage of said connector through said film cover.

4. The integrated negative pressure bandage of claim 3 wherein said drain tube is formed with a pair of opposing fluid collection tubes separated by a collector member attached to said collector.

5. The integrated negative pressure bandage of claim 3 wherein said drain tube includes a single fluid collection member with said connector being affixed to one end thereof.

6. The integrated negative pressure bandage of claim 5 wherein said drain tube is oriented diagonally to a major axis of said pad.

7. The integrated negative pressure bandage of claim 1 wherein said film cover is sized to wrap around a patient's toes with said adhesive layer sealing against both upper and lower surfaces on the patient's foot.

8. The integrated negative pressure bandage of claim 7 wherein said pad is sized to engage both the upper and lower surfaces on the patient's foot when wrapped around the patient's toes.

9. The integrated negative pressure bandage of claim 7 wherein said pad is positioned on one half of said film cover such that said pad will only engage one of the upper and lower surfaces of the patient's foot when wrapped around the patient's toes.

10. The integrated negative pressure bandage of claim 1 wherein said film cover includes:
    a rounded upper portion having an adhesive layer on a peripheral boundary portion;
    a plurality of flaps projecting outwardly from a lower portion of said film cover, said flaps including an adhesive layer; and
    a junction between said flaps to allow flexibility in movement of said flaps to seal said bandage against the patient's foot.

11. The integrated negative pressure bandage of claim 10 wherein said pad includes a rounded upper portion positioned on said upper portion of said film cover, and a rounded lower portion oriented between said flaps.

12. The integrated negative pressure bandage of claim 10 wherein said junction is one of a cutout and a perforated web.

13. The integrated negative pressure bandage of claim 1 wherein said mesh layer is impregnated with silver nitrate.

14. An integrated negative pressure bandage for removing fluid and exudates from a wound, comprising:
    a non-woven polymer matrix pad having an upper surface and a lower surface, said lower surface being positionable adjacent to and in engagement with said wound;
    a polymer film cover positioned over said upper surface of said pad and integrally secured to said upper surface of said pad to form an integral bandage therewith before being applied to said wound, said film cover including an adhesive layer on a peripheral boundary surrounding said upper portion of said pad and projecting outwardly therefrom such that said adhesive layer is operable to form a seal around said wound;
    a mesh layer integrally affixed to and covering said lower surface of and integrally secured to said polymer film cover; and
    a connector port incorporated into said film cover in flow communication with said pad, said connector port being detachably connectable to a remote vacuum pump to apply negative pressure to said pad to extract fluids and exudates from said wound through said pad to a remote location;
    a drain tube embedded into said upper surface of said pad below said film cover to be integrally incorporated into said bandage, said drain tube having a fluid collection member formed with a plurality of openings therein and being in flow communication with said pad, said drain tube being connected to said connection port for attachment to a remote vacuum pump to remove fluids and exudates from said wound through said pad; and a release member removably attached to said adhesive layer and covering said adhesive layer and said pad, said release member being an integral part of said bandage before being removed from said adhesive layer to expose said adhesive layer for utilization.

15. The integrated negative pressure bandage of claim 14 further comprising a drain tube connected to said connector port and extending across said pad to collect fluids and exudates from said wound.

16. The integrated negative pressure bandage of claim 15 wherein said drain tube is aligned with a major axis of said pad such that the connector port is centrally located on said film cover.

17. The integrated negative pressure bandage of claim 14 further comprising a release member removably attached to said adhesive layers.

18. The integrated negative pressure bandage of claim 14 wherein said film cover is formed with a plurality of flaps projecting outwardly therefrom in different directions and a junction positioned between said flaps to provide flexibility in positioning each said flap relative to the adjacent said flap, each said junction being one of a cutout and a perforated web.

19. The integrated negative pressure bandage of claim 14 wherein the mesh layer is impregnated with silver nitrate.

* * * * *